United States Patent
Staley et al.

(10) Patent No.: US 8,127,597 B2
(45) Date of Patent: *Mar. 6, 2012

(54) OIL CONDITION SENSING METHODS AND SYSTEMS

(75) Inventors: David R. Staley, Flushing, MI (US); Bryan K. Pryor, Farmington, MI (US); William C. Albertson, Clinton Township, MI (US); Timothy L. Neal, Ortonville, MI (US); Mike M. McDonald, Macomb, MI (US)

(73) Assignee: GM Global Technology Operations LLC

( * ) Notice: Subject to any disclaimer, the term of this patent is extended or adjusted under 35 U.S.C. 154(b) by 542 days.

This patent is subject to a terminal disclaimer.

(21) Appl. No.: 12/276,876

(22) Filed: Nov. 24, 2008

(65) Prior Publication Data

US 2009/0188755 A1 Jul. 30, 2009

Related U.S. Application Data

(60) Provisional application No. 61/023,954, filed on Jan. 28, 2008.

(51) Int. Cl.
*G01N 33/26* (2006.01)
*F01M 1/04* (2006.01)

(52) U.S. Cl. ............... 73/53.05; 184/6.5; 123/196 R

(58) Field of Classification Search ............... 73/53.05, 73/54.25, 54.26; 184/6.5
See application file for complete search history.

(56) References Cited

U.S. PATENT DOCUMENTS

| | | | |
|---|---|---|---|
| 3,656,140 A | 4/1972 | Gruber et al. | |
| 4,168,693 A | 9/1979 | Harrison | |
| 4,627,272 A | 12/1986 | Wright | |
| 4,637,351 A | 1/1987 | Pakula | |
| 5,381,874 A | 1/1995 | Hadank et al. | |
| 5,442,671 A | 8/1995 | Wollschlager et al. | |
| 5,808,471 A | 9/1998 | Rooke et al. | |
| 5,823,295 A | 10/1998 | Griffith et al. | |
| 5,853,068 A | 12/1998 | Dixon et al. | |
| 6,207,045 B1 | 3/2001 | Jiang | |
| 6,591,798 B2 | 7/2003 | Hendriksma et al. | |
| 7,030,580 B2 | 4/2006 | Hoff | |
| 7,178,499 B2 | 2/2007 | Wolf et al. | |
| 7,677,086 B2 | 3/2010 | Albertson et al. | |
| 2005/0022784 A1 | 2/2005 | Wolf et al. | |
| 2006/0169229 A1 | 8/2006 | Ervin et al. | |
| 2008/0093172 A1 | 4/2008 | Albertson et al. | |
| 2008/0223114 A1* | 9/2008 | Albertson et al. | 73/54.07 |
| 2008/0250851 A1* | 10/2008 | Keller et al. | 73/114.55 |
| 2008/0282786 A1 | 11/2008 | Van Weelden et al. | |
| 2010/0127718 A1 | 5/2010 | Albertson et al. | |

OTHER PUBLICATIONS

Han, T. et al., "Engine Oil Viscometer Based on Oil Pressure Sensor," SAE Technical Paper Series, 2006-01-0701, 2006 World Congress, Apr. 3-6, 2006, 9 pages.

* cited by examiner

*Primary Examiner* — Hezron E Williams
*Assistant Examiner* — Gregory J Redmann

(57) ABSTRACT

An engine oil system comprises an oil condition sensing device and a control module. The oil condition sensing device includes an electrically actuated member and is in fluid communication with an engine oil reservoir. The control module selectively causes current to be supplied to the oil condition sensing device to actuate the member, measures the current, determines a parameter of the current, and selectively identifies at least two of an oil level, an oil change event, and an oil viscosity level based on the parameter.

44 Claims, 11 Drawing Sheets

| At Shutdown | At Startup | After Cycling | Result |
|---|---|---|---|
| L | L | L | Oil Critical |
| L | L | M | Oil Low; Partial Fill Event |
| L | L | H | Fill Event |
| L | M | L | Oil Critical; Unexpected Event |
| L | M | M | Oil Low; Unexpected Event |
| L | M | H | Unexpected Event |
| L | H | L | Oil Critical; Unexpected Event |
| L | H | M | Oil Low; Unexpected Event |
| L | H | H | Unexpected Event |
| M | L | L | Oil Critical; Oil Drain Event |
| M | L | M | Oil Low; Oil Change Event |
| M | L | H | Oil Change Event |
| M | M | L | Oil Critical |
| M | M | M | Oil Low |
| M | M | H | Fill Event |
| M | H | L | Oil Critical; Unexpected Event |
| M | H | M | Oil Low; Unexpected Event |
| M | H | H | Unexpected Event |
| H | L | L | Oil Critical; Oil Drain Event |
| H | L | M | Oil Low; Oil Change Event |
| H | L | H | Oil Change Event |
| H | M | L | Oil Critical; Unexpected Event |
| H | M | M | Oil Low; Unexpected Event |
| H | M | H | Unexpected Event |
| H | H | L | Oil Critical |
| H | H | M | Oil Low |
| H | H | H | |

FIG. 11

OIL CONDITION SENSING METHODS AND SYSTEMS

CROSS-REFERENCE TO RELATED APPLICATIONS

This application claims the benefit of U.S. Provisional Application No. 61/023,954, filed on Jan. 28, 2008. The disclosure of the above application is incorporated herein by reference.

FIELD

The present disclosure relates to electrical systems and methods for engine oil measurements.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Motor oil is a type of liquid oil used for lubrication by various types of motors. In particular, internal combustion engines use motor oil to provide lubrication between mechanical components. The motor oil also cools the engine by dissipating heat generated by friction between the mechanical components.

Awareness of engine oil viscosity, engine oil levels, and engine oil change events has become increasingly important to engine control systems. This is due to recent advancements in engine control strategies that use engine oil for precise timing. Such control strategies include, for example, cam phasing, active fuel management, and two-step valve actuation. Implementing multiple systems, one for each of the detection of engine oil viscosity, the detection of engine oil levels, and the detection of an engine oil change event can be complex and expensive.

SUMMARY

An engine oil system comprises an oil condition sensing device and a control module. The oil condition sensing device includes an electrically actuated member and is in fluid communication with an engine oil reservoir. The control module selectively causes current to be supplied to the oil condition sensing device to actuate the member, measures the current, determines a parameter of the current, and selectively identifies at least two of an oil level, an oil change event, and an oil viscosity level based on the parameter.

A method comprises selectively causing current to be supplied to an oil condition sensing device to actuate a member of the oil condition sensing device; measuring the current supplied to the oil condition sensing device; determining a parameter of the current; and selectively identifying at least two of an oil level, an oil change event, and an oil viscosity level based on the parameter.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 11 is a table of exemplary determinations made for various solenoid response measurements according to the principles of the present disclosure;

DETAILED DESCRIPTION

Figure 1:
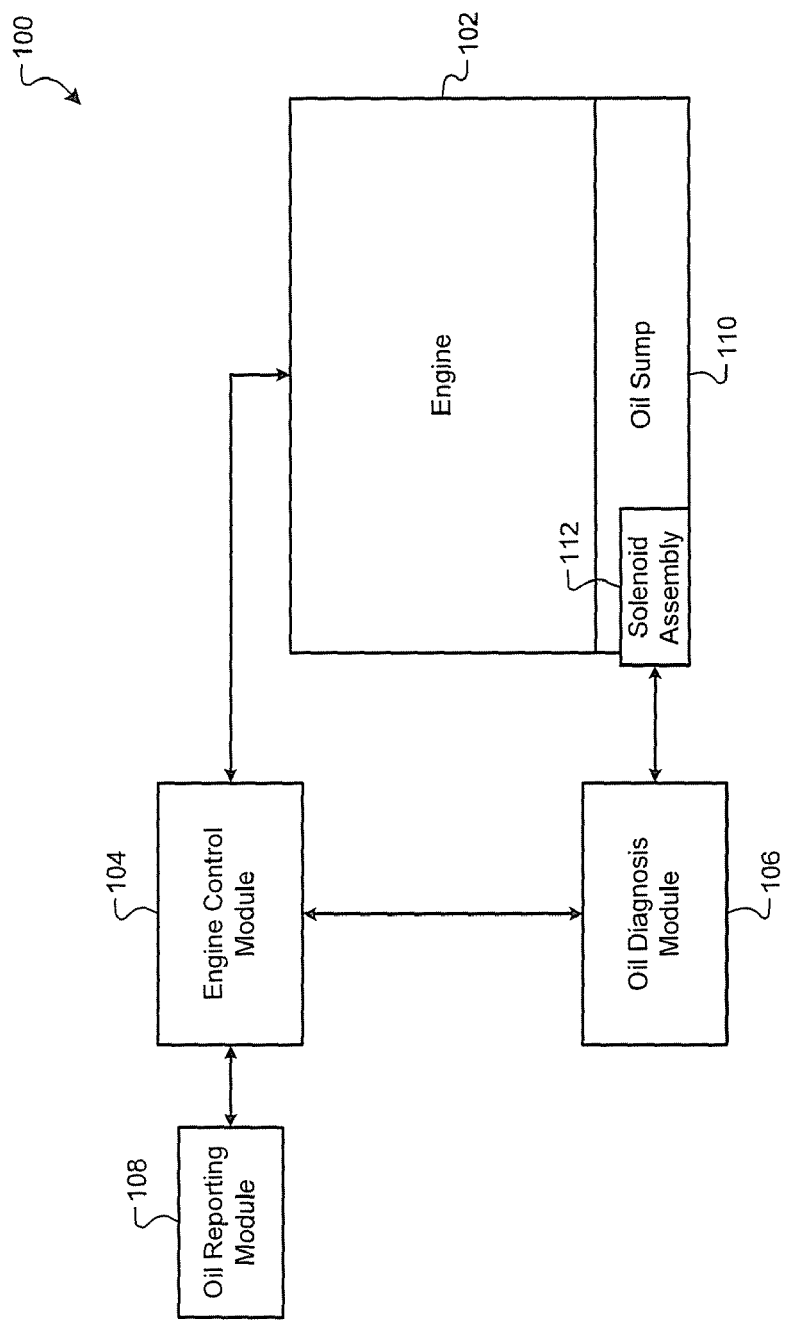
FIG. 1 is a functional block diagram of an exemplary engine system according to the principles of the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality.

Referring now to FIG. 1, a functional block diagram of an exemplary engine system 100 is presented. The engine system 100 includes an engine 102, an engine control module 104, an oil diagnosis module 106, and an oil reporting module 108. The engine control module 104 controls operation of the engine 102. For example, the engine control module 104 may control actuators (not shown) within the engine 102 to produce a torque as requested by a driver.

The engine 102 includes an oil sump 110 that stores oil used for lubricating and cooling the engine 102. The oil sump 110 may be located at the bottom of the engine 102 so that gravity returns oil to the oil sump 110. A solenoid assembly 112 measures characteristics of the oil in the engine system 100. For example only, the solenoid assembly 112 may be located within the oil sump 110.

The oil diagnosis module 106 uses the solenoid assembly 112 to determine oil conditions. As described below in FIG. 2, the current draw of a solenoid changes depending on the viscosity of the oil. The oil diagnosis module 106 may therefore be able to determine viscosity of the oil using the solenoid assembly 112. In addition, the solenoid assembly 112 may be arranged such that the solenoid interfaces with air when the oil level becomes low. This may appear as a dramatic decrease in oil viscosity. Further, the solenoid assembly 112 may be linked to a drain plug of the oil sump 110 so that the solenoid assembly 112 will recognize an oil change event.

Figure 2:
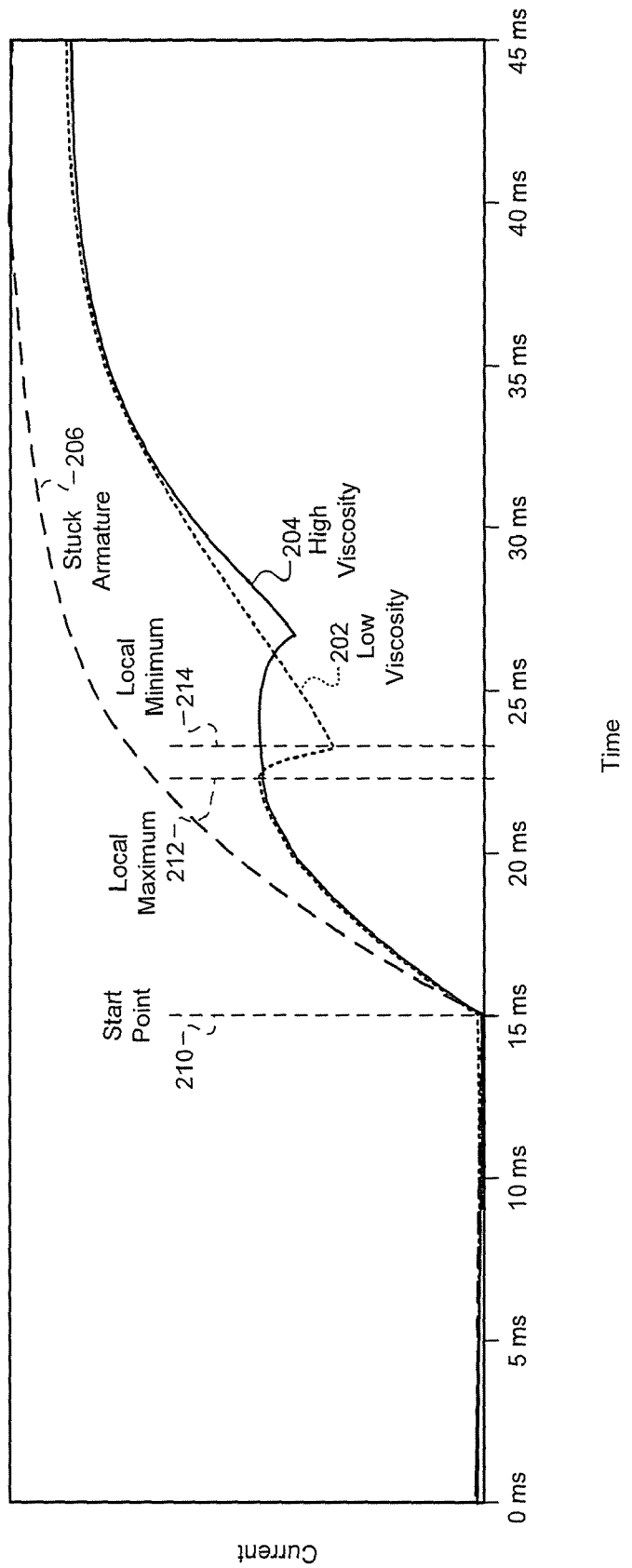
FIG. 2 graphically depicts three exemplary traces of the current of a solenoid according to the principles of the present disclosure.
Figure 3:
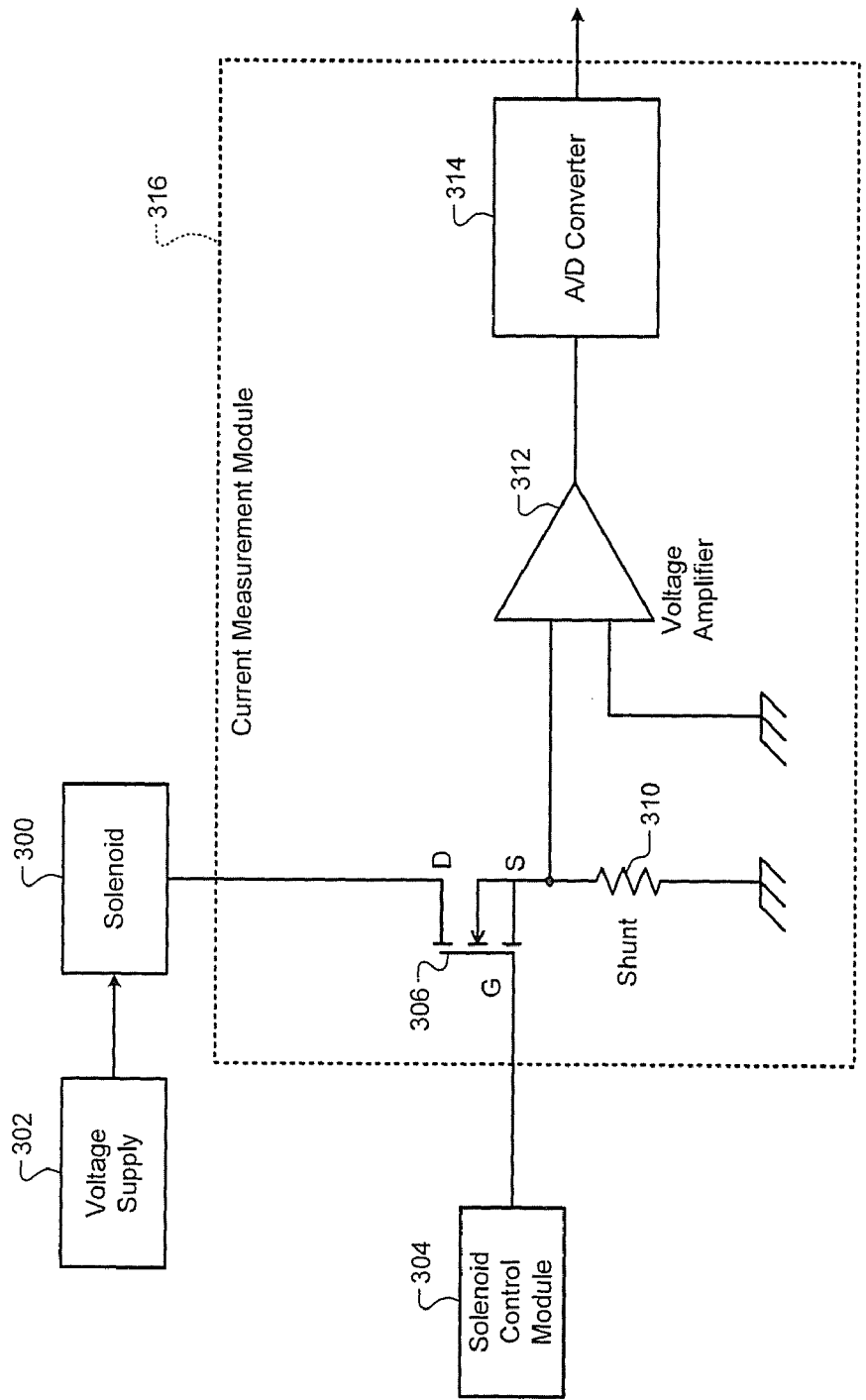
FIG. 3 is a functional block diagram of an exemplary solenoid system according to the principles of the present disclosure.
Figure 4:
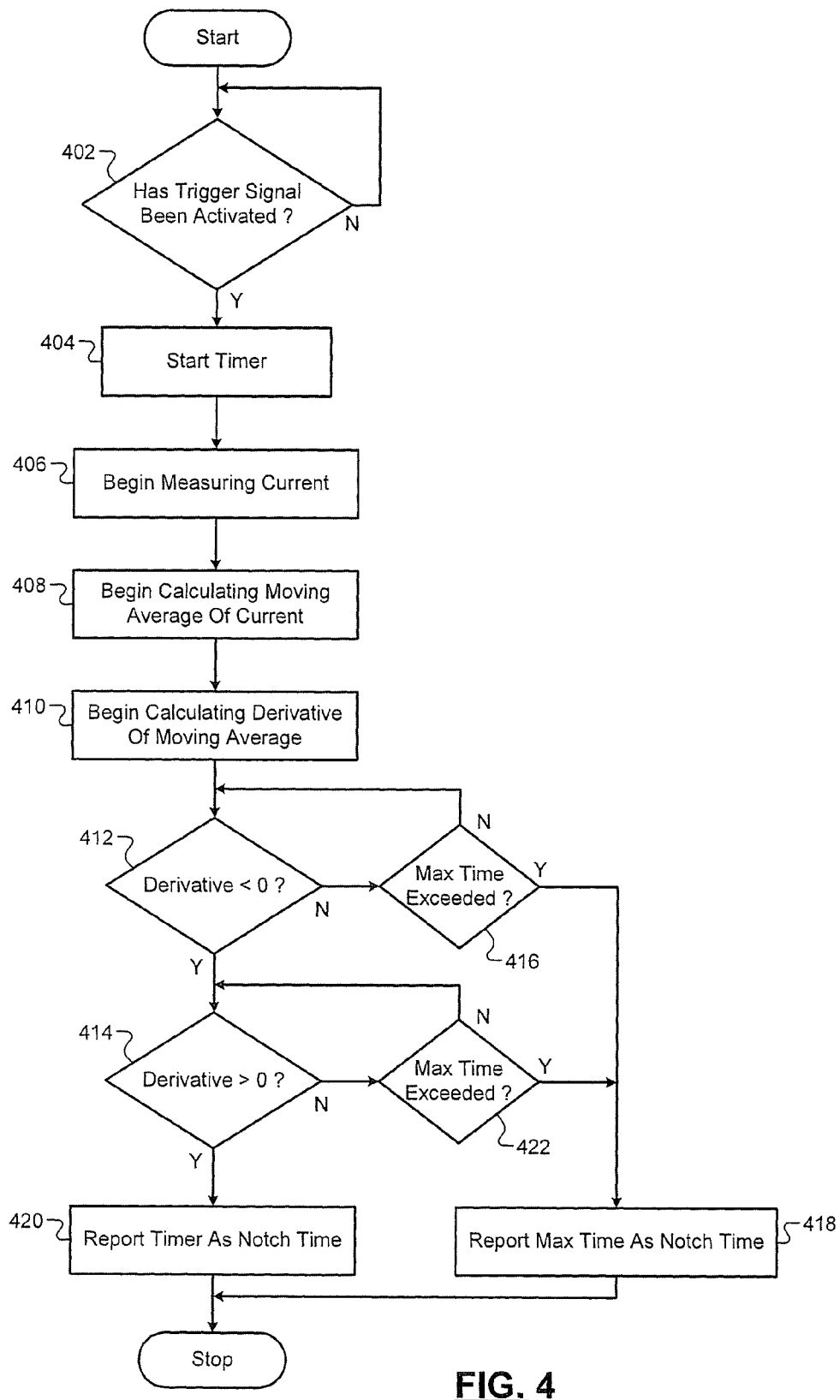
FIG. 4 is a flowchart depicting exemplary steps performed in analyzing the current signal of a solenoid according to the principles of the present disclosure.
Figure 5A:
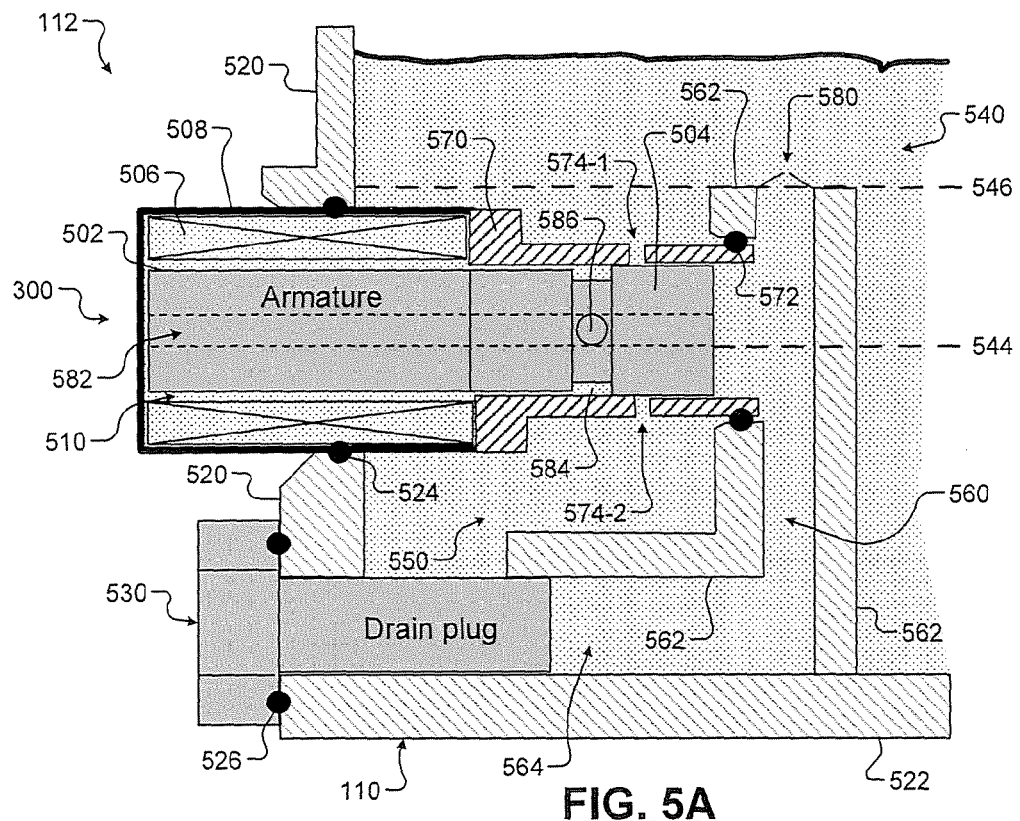
FIGS. 5A and 5B are cross-sectional views of an exemplary implementation of the solenoid assembly according to the principles of the present disclosure.
Figure 5B:
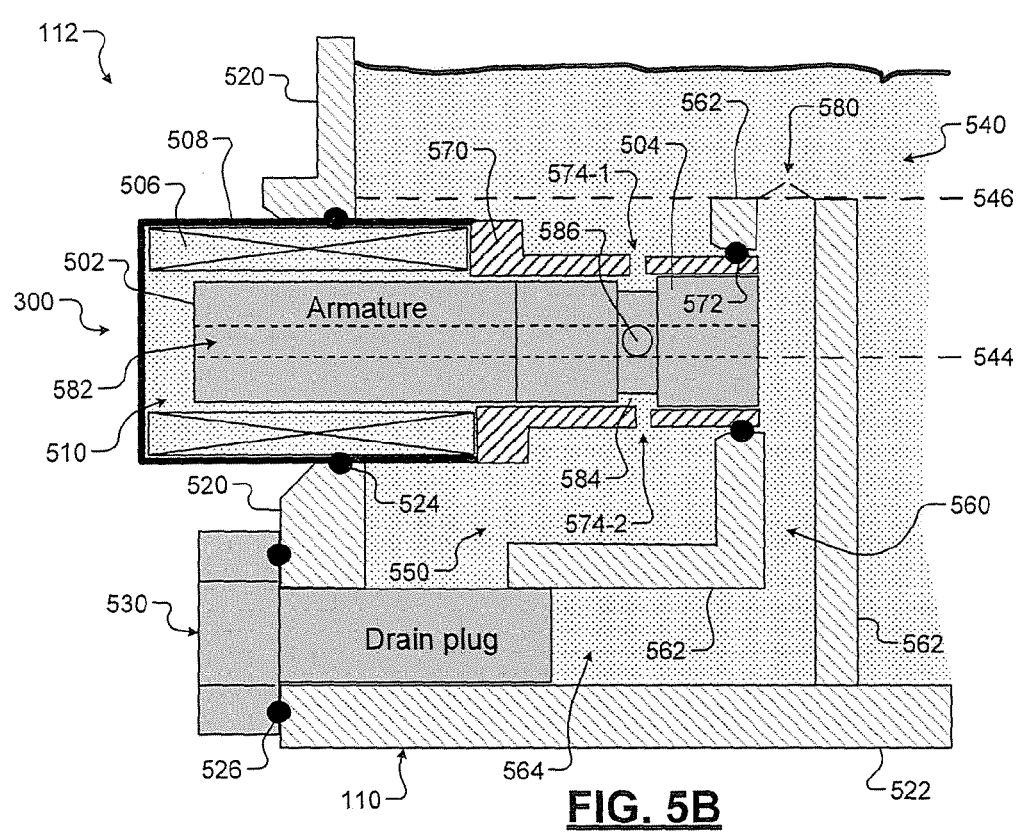

In brief, FIG. 2 depicts exemplary traces of current of a solenoid when presented with fluids having different viscosities. An exemplary system for measuring these currents is shown in FIG. 3. FIG. 4 depicts exemplary steps used to analyze the current signal to produce a number, which may be indicative of viscosity. FIGS. 5A-5B depict an exemplary implementation of the solenoid assembly 112, where a column of oil connected to the drain plug allows for detection of oil change events.

Figure 8B:
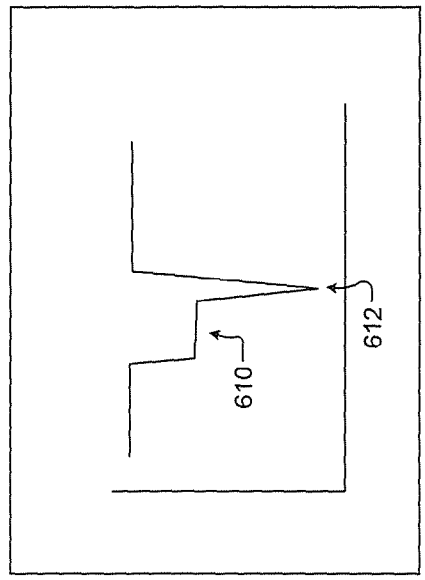
FIG. 8B shows an exemplary historical trace of solenoid notch times according to the principles of the present disclosure where an oil change was performed after the oil level had fallen below the low oil level.
Figure 9B:
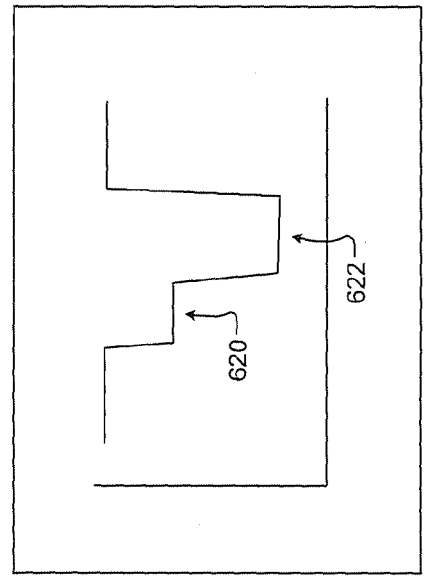
FIG. 9B shows an exemplary historical trace of solenoid notch times according to the principles of the present disclosure.
Figure 12:
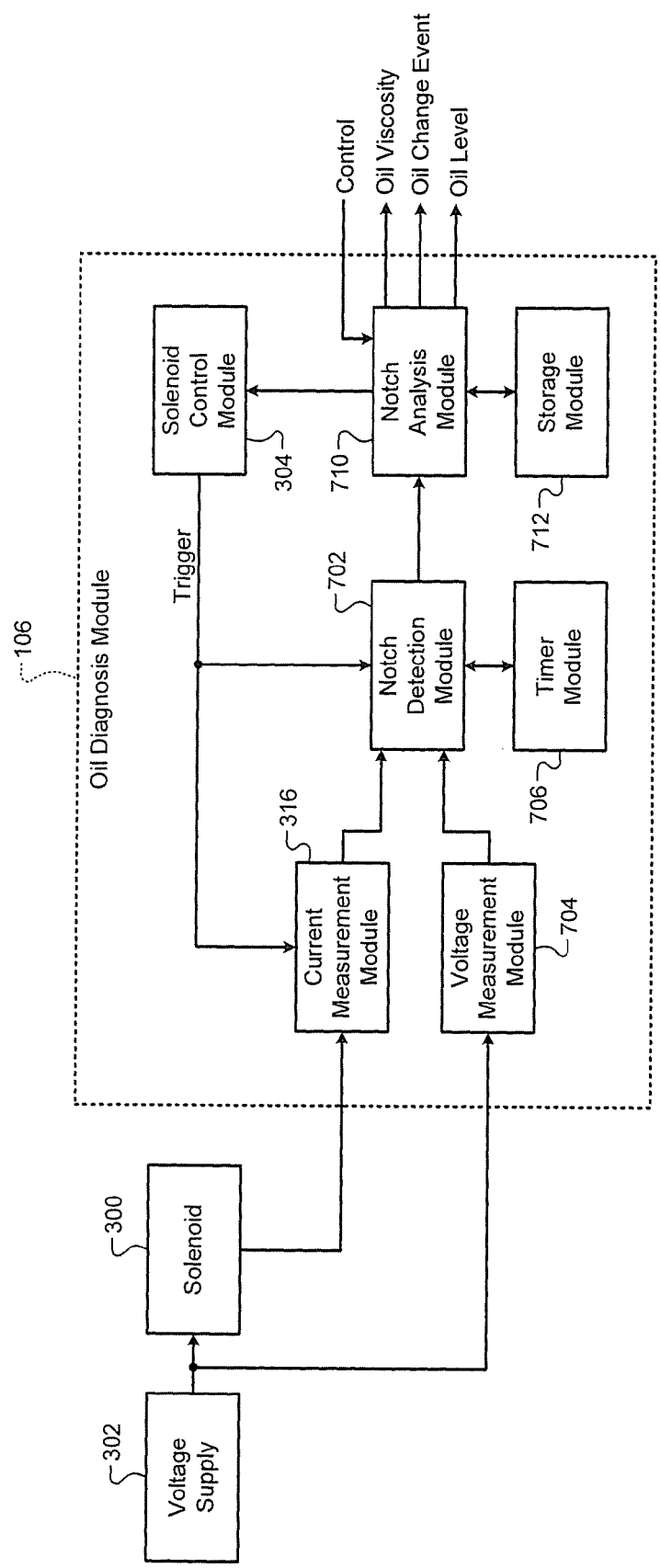
FIG. 12 is a functional block diagram of an exemplary implementation of the oil diagnosis module of FIG. 1 according to the principles of the present disclosure.
Figure 13:
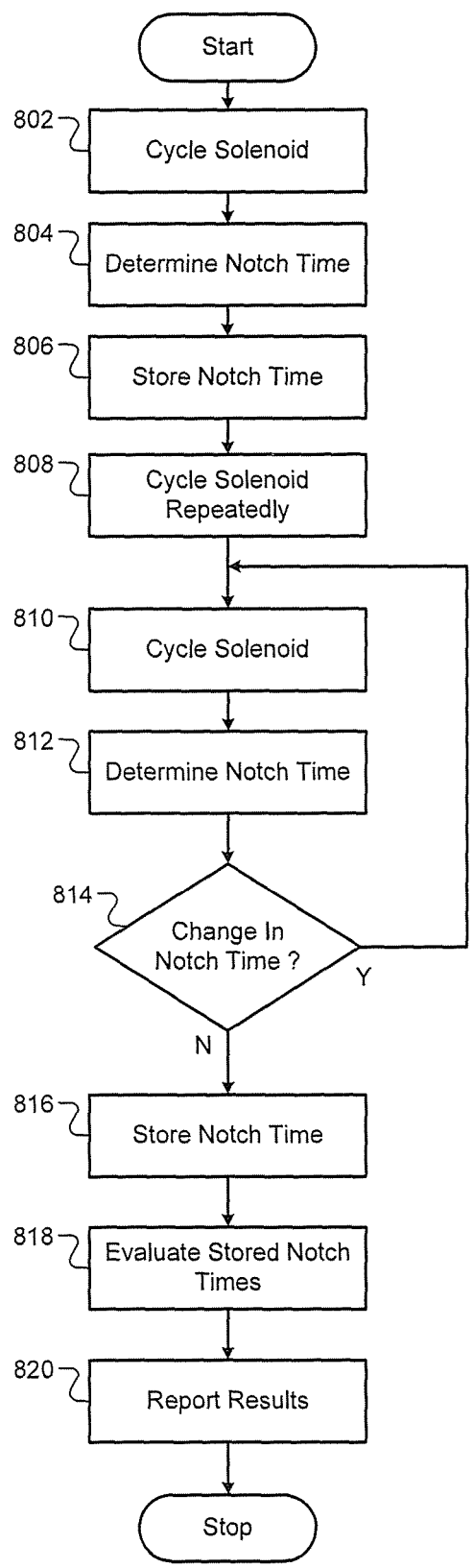
FIG. 13 is a flowchart that depicts exemplary operation of the notch analysis module of FIG. 12 according to the principles of the present disclosure.

FIGS. 6A-9B depict exemplary oil conditions measured by the solenoid assembly. FIG. 10 depicts a graph of solenoid response versus time that indicates an oil change has occurred. FIG. 11 depicts how solenoid readings can be interpreted according to one exemplary implementation. FIG. 12 is a block diagram of an exemplary implementation of the oil diagnosis module of FIG. 1, and FIG. 13 depicts exemplary steps performed by the oil diagnosis module.

Referring back to FIG. 1, the oil diagnosis module 106 provides oil status information to the engine control module 104. For example, this oil status may include oil viscosity, oil level, and detection of oil-related events. For example, the oil diagnosis module 106 may detect oil change events, oil drain events, and oil fill events. The engine control module 104 may modify operation of the engine 102 based on this information. For example, as the oil viscosity increases, the engine control module 104 may limit the speed of the engine 102.

The engine control module 104 may also report oil information to the oil reporting module 108. The oil reporting module 108 may provide visual and/or auditory indicators of oil status to the driver of the vehicle. The oil reporting module 108 may track and estimate the condition of the oil. This estimation may be based upon the number of miles driven since the last oil change. The estimation may be adjusted based on measured oil viscosity from the oil diagnosis module 106.

When an oil change has been performed, this event may be reported to the oil reporting module 108 by a driver or technician through a user interface. This user interface may be multiplexed with other vehicle controls, such as odometer and/or clock controls. Inadvertent indications of an oil change to the oil reporting module 108 may be identified by comparing user entered data to oil change events detected by the oil diagnosis module 106. Alternatively, the oil reporting module 108 may ignore user input and determine oil change events based on data from the oil diagnosis module 106. The oil reporting module 108 may indicate to the driver that an oil change is needed.

Referring now to FIG. 2, three exemplary traces 202, 204, and 206 of the current of a solenoid are shown. Trace 202 corresponds to a low viscosity, trace 204 corresponds to a higher viscosity, and trace 206 corresponds to an infinite viscosity. An infinite, or extremely high, viscosity has the same effect as if the armature of the solenoid were mechanically stuck. Traces 202 and 204 each include a notch in the current. By contrast, trace 206 lacks the notch. For traces similar to trace 206, the notch time may be considered to be infinite, or set to a maximum amount of time.

The location of the notch is an indication of the viscosity of the fluid with which the solenoid is interfacing. Because the solenoid piston displaces fluid in front of the piston, hydraulic resistance is caused by the viscous oil moving through restrictive oil flow passages (such as one or more orifices). This hydraulic resistance exerts a pressure on the face of the piston, which resists armature movement and changes the current response characteristics of the solenoid.

At a start point 210, the solenoid is instructed to actuate. This may be initiated by a trigger signal that arrives at the start point 210. For purposes of illustration, trace 202 will be analyzed. After the start point 210, the current of trace 202 begins increasing. At a first point 212, trace 202 transitions from increasing to decreasing. The first point 212 is therefore a local maximum.

Trace 202 then decreases until a second point 214, when trace 202 transitions from decreasing back to increasing. The second point 214 is therefore a local minimum. The armature of the solenoid begins moving at the first point 212 and stops moving at the second point 214. The measured current between the first and second points 212 and 214 decreases because the moving armature creates a back electromotive force (EMF) that opposes the electrical potential. The amount of time elapsed between the start point 210 and the second point 214 is referred to as the notch time. The notch time of trace 202 is less than the notch time of trace 204, indicating that the solenoid is interfacing with a higher viscosity fluid in trace 204. The notch time of trace 206 may be set to a predetermined maximum value. For example, the notch time for trace 206 may be set to 45 ms.

Referring now to FIG. 3, a functional block diagram of an exemplary solenoid system is presented. A solenoid 300 receives power from a voltage supply 302. For example only, the voltage supply 302 may provide a constant voltage to the solenoid 300. The current from the voltage supply 302 may be limited to prevent damage to the solenoid 300.

A solenoid control module 304 controls when the solenoid 300 is actuated. In various implementations, the solenoid 300 may include a spring that displaces an armature of the solenoid 300 to a first position. By providing a current through windings of the solenoid 300, electromagnetic force generated by current can displace the armature against the spring to a second position. When the current is removed, the armature may return to the first position by action of the spring.

The solenoid control module 304 may activate a switch 306 in order to actuate the solenoid 300. The switch 306 may conduct current between the solenoid 300 and a reference potential, such as ground. When current is flowing through the switch 306, the solenoid 300 may be considered actuated, with the armature at the second position.

For example only, the switch 306 may include an n-channel metal oxide semiconductor field effect transistor (MOSFET). The transistor may include a control terminal (labeled G or gate) and first and second terminals (labeled D and S for drain and source, respectively). The control terminal may be connected to the solenoid control module 304, the first terminal may be connected to the solenoid 300, and the source terminal may be connected to the reference potential via a shunt resistor 310.

Current flowing through the solenoid 300 therefore flows through the resistor 310, creating a voltage drop across the resistor 310 that is proportional to the amount of current. This voltage drop may be measured by a voltage amplifier 312, which may be referenced to the same reference potential. Alternatively, any other system for sensing current may be used, such as a Hall effect sensor.

An amplified version of the input voltage is output from the voltage amplifier 312 to an analog-to-digital (A/D) converter 314. The A/D converter 314 digitizes the output of the voltage amplifier 312 and outputs a digital signal. This digital signal can then be analyzed to determine the notch time of the solenoid's current. A current measurement module 316 may include the switch 306, the resistor 310, the voltage amplifier 312, and the A/D converter 314.

Referring now to FIG. 4, a flowchart depicts exemplary steps performed in analyzing the current signal from the current measurement module 316 of FIG. 3. Control begins in step 402, where control determines whether the trigger signal has been activated. If so, control continues in step 404; otherwise, control remains in step 402. In step 404, a timer is started and control continues in step 406.

In step 406, control begins measuring current through the solenoid. Control continues in step 408, where control begins calculating a moving average of the current. In order to prevent a false detection of a local maximum or local minimum, control may calculate a moving average of the current. In this way, small disturbances in the current signal, such as those due to noise, will not be incorrectly detected as a change in slope of the overall line.

For example only, the moving average may be a two-point moving average. The moving average may be calculated as a prior moving average or as a central moving average, which uses data taken after the point being calculated. In addition, the moving average may be a simple moving average or a weighted moving average, where the weighting may be linear or exponential.

Control continues in step 410, where control begins calculating a derivative of the moving average. For example only, control may calculate the derivative as the difference between the current moving average value and the previous moving average value divided by the time between the moving average values. Control continues in step 412, where control determines whether the derivative has decreased below 0. If so, control transfers to step 414; otherwise, control transfers to step 416. For example only, control may transfer to step 414 only when multiple sequential derivatives remain below 0.

In step 416, control determines whether the timer is greater than a predetermined maximum time. If so, control transfers to step 418; otherwise, control returns to step 412. In step 414, control determines whether the derivative has returned above 0 after being below 0 in step 412. If so, control transfers to step 420; otherwise, control transfers to step 422. As in step 412, control may evaluate multiple derivatives in step 414 to ensure that the derivative has stably increased above 0. In step 422, control determines whether the timer has exceeded the predetermined maximum time. If so, control transfers to step 418; otherwise, control returns to step 414. In step 420, control reports the timer value as the notch time and control stops. In step 418, control reports the predetermined maximum time as the notch time and control stops.

Referring now to FIG. 5A, a cross-sectional view of an exemplary implementation of the solenoid assembly 112 is shown. The solenoid assembly 112 includes the solenoid 300. The solenoid 300 includes an armature 502, a piston 504, windings 506, and a casing 508. The casing 508 defines a chamber 510. The armature 502 is held in the chamber 510 via a spring (not shown).

The solenoid 300 is inserted into a wall 520 of the oil sump 110. The wall 520 is joined to a base 522 of the oil sump 110. The seal between the solenoid 300 and the wall 520 may be maintained by an o-ring 524. A drain plug 530 may be inserted into an opening of the wall 520. The opening may be sealed against the drain plug 530 by an o-ring 526. Oil in the oil sump 110 is indicated by shading, such as in spaces indicated by reference numerals 540 and 550. The oil in the space 540 in the oil sump 110 is in fluid communication with the oil in the space 550. The space 550 is open to the space 540, although this connection is not visible in this cross-sectional view.

Levels of oil in the oil sump 110 may be defined. For example, a critical oil level 544 may be defined. If the level of oil in the oil sump 110 falls below the level 544, the oil may be considered to be critically low. A low oil level 546 may also be defined. If the oil level is below the level 546 but above the level 544, the oil level may be identified as low. A captive space 560 of oil may be defined by an enclosure 562. The enclosure 562 may be cylindrical, making the captive space 560 a column. The enclosure 562 includes an opening at its bottom that connects to a horizontal channel 564. The horizontal channel 564 is not open to the space 550 while the drain plug 530 is fully inserted.

The enclosure 562 also has an opening for the solenoid 300. The solenoid 300 may include a sleeve 570 within which the piston 504 rides. The end of the sleeve 570 is inserted into the enclosure 562, and may be sealed by an o-ring 572. The sleeve may include one or more holes. For example only, the sleeve 570 is shown having two openings, 574-1 on top and 574-2 on bottom.

At the top of the enclosure 562 is an orifice 580. When the oil level in the enclosure 562 is above the level 546, oil will cover the orifice 580. A second orifice 582 is opened axially through the armature 502 and the piston 504. The second orifice 582 thereby fluidically couples the captive space 560 to the chamber 510. If the oil level in the enclosure 562 is above the level 544, the second orifice 582 will be submerged in oil.

A recess 584 is formed in the piston 504. The recess 584 may wrap around the circumference of the piston 504. The recess 584 is fluidically coupled to the second orifice 582 via an opening 586. The opening 586 may be orthogonal to the second orifice 582.

Referring now to FIG. 5B, when the solenoid 300 is actuated, the armature 502 moves out of the chamber 510. The piston 504 forces oil through the orifice 580 as well as the second orifice 582. If the fluid immediately below the orifice 580 is air instead of oil, the viscosity seen by the solenoid 300 will be reduced. If air is present below the orifice 580, the type of fluid (such as air or oil) above the orifice 580 may have an insignificant effect on the measured viscosity. If the oil level is below the level 544 when the solenoid 300 actuates, the second orifice 582 will be filled with air and the resistance seen by the solenoid 300 will be even lower still.

When both orifices 580 and 582 are submerged in oil, actuation of the solenoid 300 can be used to determine the viscosity of that oil. In order to obtain a representative sample of the oil in the oil sump 110, the solenoid 300 may be left in the actuated position. In this way, the captive space 560 within the enclosure 562 is fluidically coupled to the remainder of the oil sump 110, such as the spaces 540 and 550. This fluidic coupling is accomplished through openings 574-1 and 574-2, the opening 586, the piston 504, and the second orifice 582. The solenoid 300 may be actuated repeatedly to agitate the oil and promote mixing of the oil. In addition, the solenoid 300 may act as a pump in pumping oil between the space 540 of the oil sump 110 and the captive space 560.

When the drain plug 530 is removed, the oil in the oil sump 110, including the space 540 and the captive space 560, can be drained through the opening in the wall 520. When the drain plug 530 is replaced, air is trapped within the captive space 560. The small size of the orifice 580 and the surface tension of the oil may prevent oil from refilling the captive space 560 when the oil sump 110 is filled.

Therefore, after an oil change, the captive space 560 is filled with air while the remaining space 540 of the oil sump 110 is filled with oil. Actuating the solenoid 300 may therefore initially produce a low viscosity reading. However, if the solenoid 300 is actuated repeatedly, oil will fill the captive space 560. The viscosity reading will then become that of the oil. An oil change event may therefore be detected by a normal viscosity prior to engine shutdown and a low viscosity upon engine startup that transitions to a normal viscosity once again. This and other scenarios are described in FIGS. 6A-9B, and an exemplary summary of detected conditions is shown in FIG. 11.

Figure 6A:
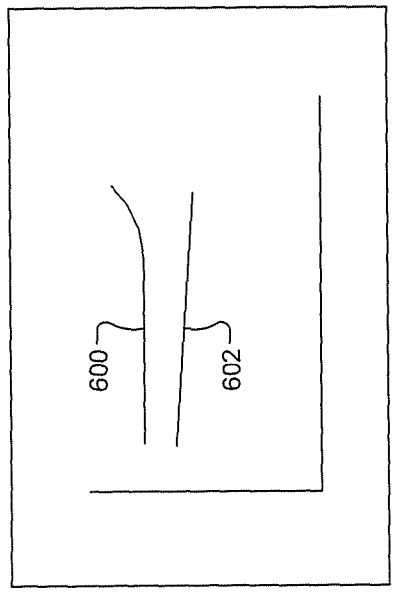
FIG. 6A is a cross-sectional view graphically illustrating a solenoid according to the principles of the present disclosure when the oil level is above the low oil level.
Figure 6B:
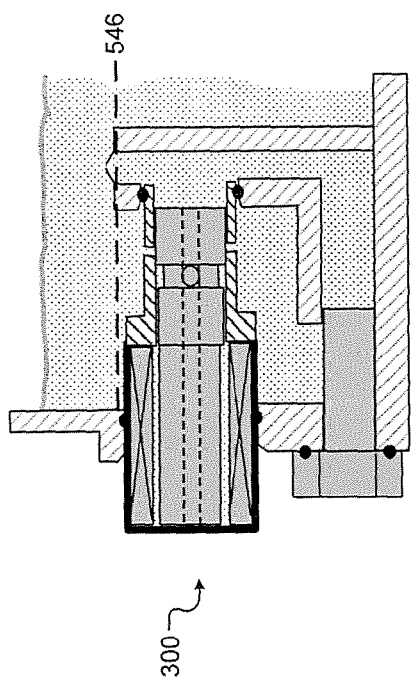
FIG. 6B shows exemplary historical traces of solenoid notch times according to the principles of the present disclosure.

Referring now to FIG. 6A, a cross section graphically illustrates the solenoid 300 when the oil level is above the low oil level 546. The solenoid 300 is therefore measuring viscosity of the oil. FIG. 6B shows exemplary historical traces of solenoid actuation. For example only, solenoid readings may be performed each time the vehicle is turned on. First and second traces 600 and 602 may correspond to two different vehicles and are plotted on a plane of notch delay versus time. The graphs shown in FIGS. 6B, 7B, 8B, and 9B may encompass many engine key-on cycles.

The notch delay is the time from when the solenoid is commanded to actuate until the notch is measured. The notch time increases as viscosity of the oil increases. As shown in FIG. 6B, trace 600 shows viscosity that slowly increases over time and then begins to increase more rapidly. This may be a sign of impending oil failure, and may be signaled as an error condition. Trace 602 shows a fairly flat trend in oil viscosity, although the oil viscosity is slowly decreasing. At a certain point, a low enough oil viscosity may no longer provide necessary lubrication for engine components, and an error condition may be signaled.

Figure 7A:
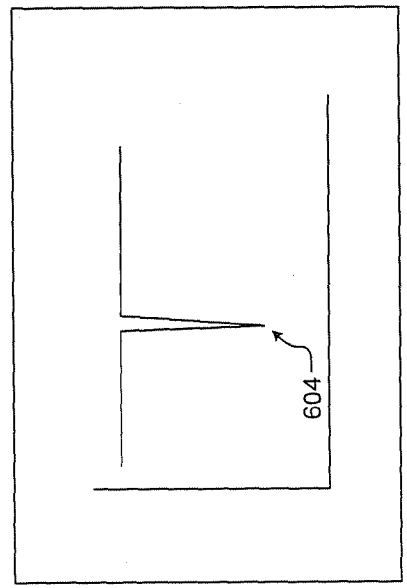
FIG. 7A is a cross-sectional view graphically illustrating a solenoid according to the principles of the present disclosure after an oil change.
Figure 7B:
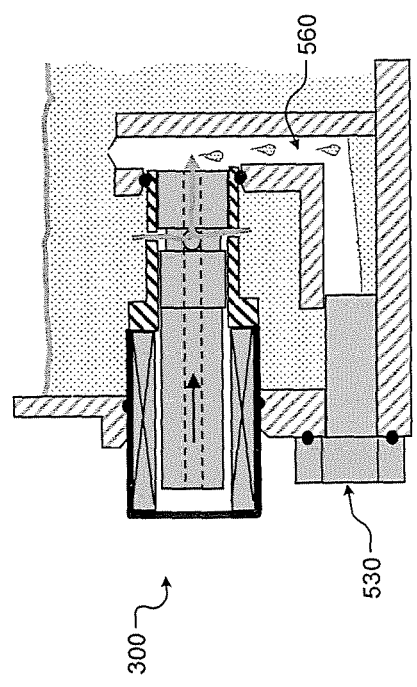
FIG. 7B shows an exemplary historical trace of solenoid notch times according to the principles of the present disclosure.

Referring now to FIG. 7A, a cross section graphically illustrates a filling of the captive space 560 after an oil change. Because the drain plug 530 is replaced before oil is refilled, air is trapped within the captive space 560. By actuating the solenoid 300 one or more times, the captive space 560 is filled with oil. FIG. 7B shows a historical chart of notch delay time. A sudden drop in notch delay time is seen at 604. The notch delay time then quickly returns to the normal level. This may be an indication that an oil change event has occurred.

Figure 8A:
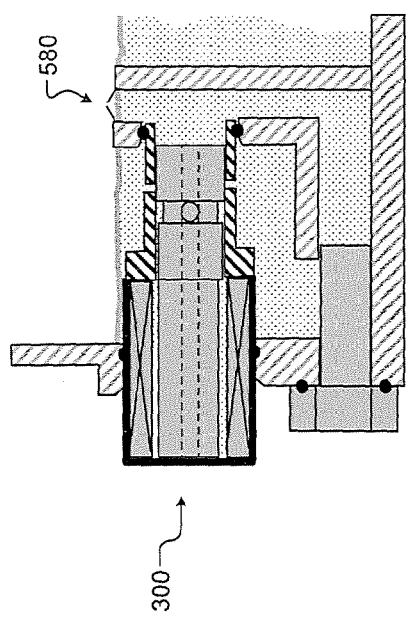
FIG. 8A is a cross-sectional view graphically illustrating a solenoid according to the principles of the present disclosure when the oil level is below the low oil level.

Referring now to FIG. 8A, a cross section graphically illustrates when oil is below the low oil level. The oil is no longer present directly below the orifice 580. Therefore, when the solenoid 300 is actuated, air is forced through the orifice 580 instead of oil, and the resulting viscosity measurement is lower. This lower level is shown in FIG. 8B at 610. FIG. 8B also indicates that an oil change occurred at 612 after the engine oil had been low for a period of time.

Figure 9A:
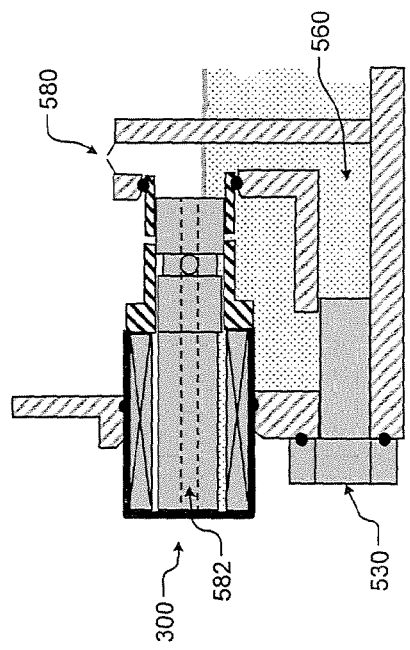
FIG. 9A is a cross-sectional view graphically illustrating a solenoid according to the principles of the present disclosure when the oil level is below the critical oil level.
Figure 10:
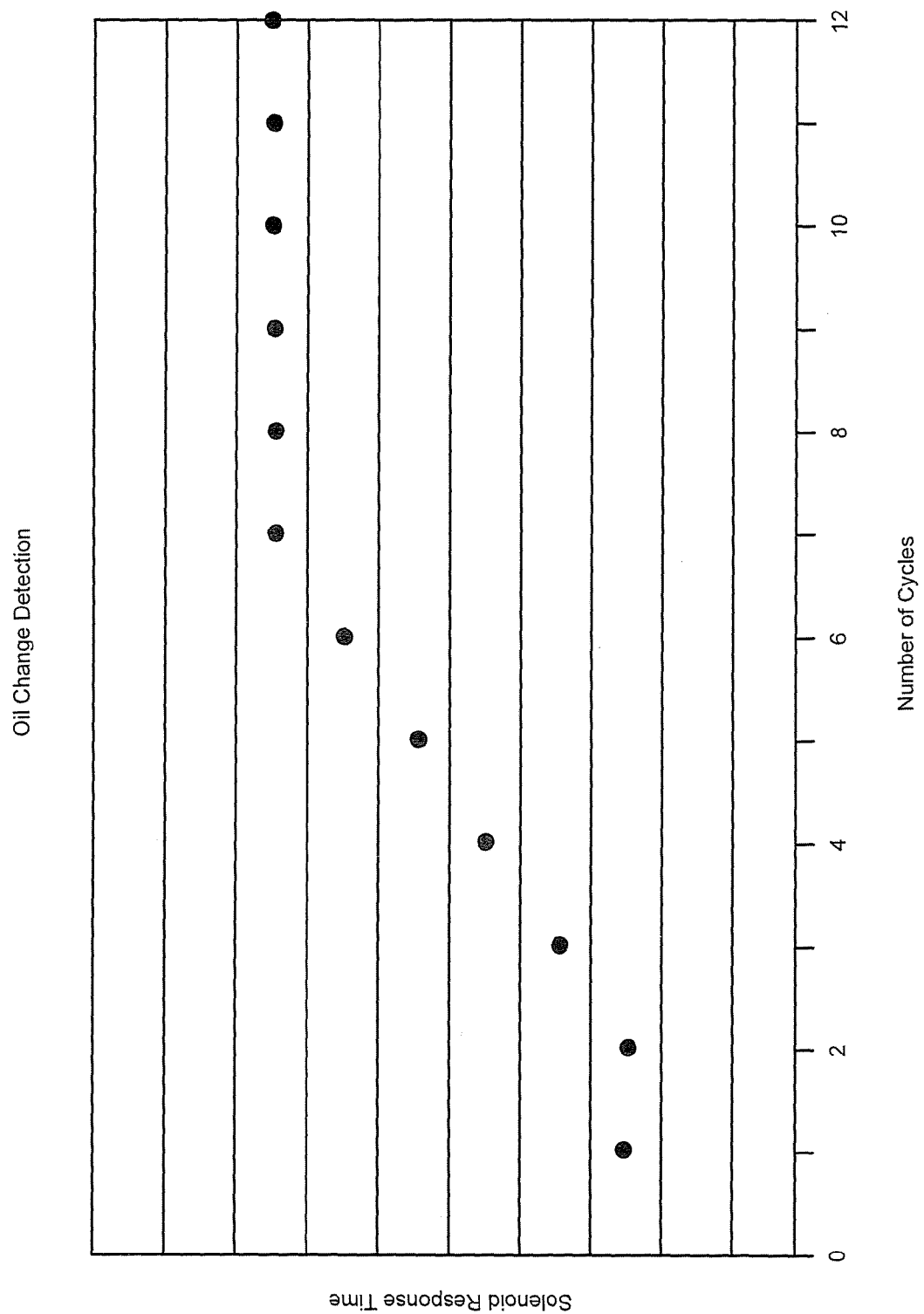
FIG. 10 is a graphical illustration of notch delay times over a number of solenoid cycles according to the principles of the present disclosure that indicate an oil change event.

Referring now to FIG. 9A, a cross section graphically illustrates a critically low oil level. Because the oil is at a critically low level, the orifice 580 is exposed to air, and the second orifice 582 is no longer submerged in oil. This will result in a low viscosity being experienced by the solenoid 300. FIG. 9B shows a period 620 of low oil followed by a period 622 of critically low oil. When the oil returns to a normal viscosity, it may be assumed that an oil change has been performed.

However, it is possible that the oil sump 110 has simply been filled. It may be possible to distinguish between these two scenarios by monitoring the rate at which, or the time during which, the measured viscosity increases. If the drain plug 530 had been removed, it would take longer for the captive space 560 to fill with oil. However, if the oil sump 110 has simply been filled with oil, the captive space 560 may already contain oil. This will lead to a faster increase in viscosity measurements as the solenoid 300 can quickly fill the remainder of the captive space 560.

Referring now to FIG. 10, a graphical illustration of notch delay times over a number of solenoid cycles is presented. At cycle 1, a fairly low solenoid response (or, notch delay time) is measured. Approximately the same time is measured at the second cycle. By the third cycle, the notch delay time has begun increasing. At cycle seven, the notch delay time approximately levels out for the remainder of the 12 cycles. This response may be characteristic of an oil change event. At cycle seven, the cylinder of oil is once again refilled and the solenoid response time will be a reflection of the viscosity of the oil.

Referring now to FIG. 11, a table depicts exemplary determinations made for various solenoid response measurements. In the first column, the solenoid measurement made at or before engine shutdown is shown. In the second column, the solenoid measurement made after engine startup is shown. This measurement may be made during engine startup or at some later time during operation of the vehicle.

The third column shows a solenoid measurement taken after the solenoid has been cycled multiple times. In the fourth column, the interpretations of the respective solenoid measurements are presented. The three solenoid measurements depicted in FIG. 11 are low (L), medium (M), and high (H). A low measurement signifies a low level of oil in the captive space 560. This corresponds to the orifice 580 and the second orifice 582 interfacing with air, which results in a low notch delay time.

A medium measurement corresponds to the second orifice 582 containing oil while the orifice 580 is exposed to air. This will produce a solenoid response higher than that of the low level. A high measurement corresponds to the orifices 580 and 582 both being submerged in oil. This will produce the highest notch delay time. This is detected as a normal oil level; the oil sump 110 may not be completely full, but the level is greater than the low oil level.

The condition where the orifice 580 is exposed to oil while the second orifice 582 is exposed to air may indicate an error condition. Although the top of the orifice 580 may be covered by oil, if the fluid below the orifice 580 is air, the air will be pressed through the orifice 580, thereby determining the solenoid response. Therefore, in order to detect oil for the orifice 580 and air for the second orifice 582, oil would need to be suspended below the orifice 580 while air was trapped in front of the piston 504. This condition may be assumed to not occur in normal operation.

The first nine rows after the header in FIG. 11 correspond to a low level of oil during the last engine shutdown. If engine oil is low upon startup and remains low, an oil critical signal may be produced. If the oil measurement is low at startup and transitions to medium, the oil is still low, but a partial fill event has been detected.

It is possible that an oil change has been performed. However, it is less likely because after an oil change the oil level should be high. If the response time is low and transitions to high, a fill event is detected. Again, an oil change may have been performed. As described above, the amount of time consumed in transitioning from a low response to a high response may determine whether the oil has been changed or simply filled.

If the response at startup is medium and transitions to low, the oil critical signal may be generated. However, this may be an unexpected scenario. For the remaining rows where the response was low at shutdown, an unexpected event may be detected. Because the response was low at shutdown and the captive space 560 should remain closed off from additional oil, detection of a medium or high response upon startup may be anomalous.

The next nine rows correspond to a medium response prior to engine shutdown. If, upon startup, the response is low, it may be inferred that the drain plug 530 was removed. If the solenoid response does not transition away from low, however, the oil level is still critical. In this case, the oil may have been drained without adding additional oil.

If the solenoid response transitions from low to medium, an oil change event is apparent. However, the oil was not fully refilled. This may also indicate an unexpected scenario. If the solenoid response transitions to high, a normal oil change event is detected. If, upon startup, the response is medium and transitions to low, this could be the result of normal oil loss. The oil level is now critical.

If the response stays at medium, the oil level is low. If the solenoid response transitions to high, the oil sump 110 may have been filled to correct the low oil condition. If the response upon startup is high when the response prior to shutdown is medium, this may represent an unexpected event.

The final set of nine rows corresponds to a high response prior to engine shutdown. At startup, if the response is low and remains low, it appears that the oil has been drained. If the response transitions from low to medium, an oil change event has occurred. However, the oil has not been completely refilled. If the response transitions from low to high, a normal oil change event is detected. If the response upon startup is medium and the response at shutdown was high, this may represent an unexpected event. A leak may have occurred somewhere within the solenoid assembly 112, for example.

If the response begins at high and transitions to low, the oil level is critical. Similarly, if the response transitions to medium, the oil level is low. If the response remains at high, the oil level appears to be acceptable and no events have been detected. In each of the cases where the response after cycling is high, oil viscosity may be measured.

Referring now to FIG. 12, a functional block diagram of an exemplary implementation of the oil diagnosis module 106 is presented. The oil diagnosis module 106 may include the current measurement module 316. The current measurement module 316 provides measurements of current flowing through the solenoid 300 to a notch detection module 702.

A voltage measurement module 704 may measure the voltage being output by the voltage supply 302. The voltage measurement module 704 provides this voltage information to the notch detection module 702. The solenoid control module 304 may control the solenoid 300 or may actuate a switch, which selectively allows current to flow through the solenoid 300. For example only, the switch may be located within the current measurement module 316.

A trigger signal from the solenoid control module 304 activates the switch within the current measurement module 316, thereby actuating the solenoid 300. The trigger signal is also received by the notch detection module 702. Upon receiving the trigger signal, the notch detection module 702 may initialize a timer in a timer module 706. The notch detection module 702 determines the delay time of the current notch, as described in FIGS. 2-4. The notch delay time is provided to a notch analysis module 710.

The notch analysis module 710 may instruct the solenoid control module 304 to actuate the solenoid 300 one or more times. The notch analysis module 710 may store calibration data in a storage module 712. For example, the calibration data may indicate what ranges of notch delay times fall within response categories, such as high, medium, and low. The notch analysis module 710 may receive control signals from the engine control module 104, and may provide oil viscosity level, oil level, and oil change event information to the engine control module 104.

Because oil viscosity may increase as oil temperature increases, the notch analysis module 710 may normalize the oil viscosity level to a reference oil temperature. For example only, the oil temperature may be measured directly, modeled, and/or inferred from other temperature measurements, such as engine coolant temperature. In various implementations, viscosity values may be stored in a lookup table indexed by oil temperature and notch delay time. The values in the lookup table may be determined empirically or estimated based on solenoid characteristics, such as orifice and piston geometries.

The notch detection module 702 may use voltage information from the voltage measurement module 704 to scale values from the current measurement module 316. In addition, the notch delay time may be adjusted based upon the voltage. For example only, a higher voltage from the voltage supply 302 may decrease the notch delay time. The notch detection module 702 may therefore increase the indicated notch delay time when the voltage is higher.

Referring now to FIG. 13, a flowchart depicts exemplary operation of the notch analysis module 710 of FIG. 12. Control begins in step 802, where the solenoid is cycled. Control continues in step 804, where the notch time is determined. Control continues in step 806, where the notch time is stored. Control continues in step 808, where the solenoid is cycled a predetermined number of times. For example, the solenoid may be cycled enough times to fill the volume of the captive space 560 with oil from the remaining portion of the oil sump 110.

Control continues in step 810, where the solenoid is cycled one or more times. Control continues in step 812, where the notch time is determined. Control continues in step 814, where control determines whether there is a change in notch time from the previous measurement. If so, control returns to step 810 to continue cycling the solenoid until the notch time stabilizes. Otherwise, control transfers to step 816. In step 816, the notch time is stored.

Control continues is step 818, where the stored notch times are evaluated. The stored notch times include the notch times stored after the first cycle in step 806, as well as the notch time stored in step 816 after the notch time stabilized. The stored notch times may also include notch times stored from previous engine runs, such as the last notch time determined before the engine shut down. This evaluation may be performed using a table, such as that depicted in FIG. 11. Control continues in step 820, where the results are reported. Control then stops.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. An engine oil system comprising:
    an oil condition sensing device that includes an electrically actuated member, wherein the oil condition sensing device is in fluid communication with an engine oil reservoir; and
    a control module that selectively causes current to be supplied to the oil condition sensing device to actuate the member, that measures the current, that determines a parameter of the current, and that selectively identifies at least two of an oil level, an oil change event, and an oil viscosity level based on the parameter.

2. The engine oil system of claim 1 wherein the parameter is based on a time of a local minimum of the current while the member is actuating.

3. The engine oil system of claim 2 wherein the parameter is based on a time delay between a trigger time and the time of the local minimum, wherein the control module causes current to be supplied to the oil condition sensing device at the trigger time.

4. The engine oil system of claim 1 wherein the member is actuated to a first position when current is supplied and returns to a second position when current is not supplied.

5. The engine oil system of claim 1 wherein the oil level represents an oil level of the engine oil reservoir.

6. The engine oil system of claim 1 wherein the oil viscosity level represents an oil viscosity level of a sample of oil from the engine oil reservoir.

7. The engine oil system of claim 1 wherein the oil condition sensing device includes first and second orifices, and wherein when the member is actuated, a first fluid is forced through the first orifice and a second fluid is forced through the second orifice.

8. The engine oil system of claim 7 wherein the control module determines that the first fluid is one of air and oil and that the second fluid is one of air and oil based on the parameter.

9. The engine oil system of claim 8 wherein the first orifice is positioned higher than the second orifice.

10. The engine oil system of claim 9 wherein the control module identifies the oil level as below a first predetermined level when the second fluid is air.

11. The engine oil system of claim 10 wherein the control module identifies the oil level as between the first predetermined level and a second predetermined level when the first fluid is air and the second fluid is oil, wherein the second predetermined level is greater than the first predetermined level.

12. The engine oil system of claim 11 wherein the control module identifies the oil level as above the second predetermined level when the first fluid and second fluids are oil.

13. The engine oil system of claim 8 wherein the control module determines a state of the oil condition sensing device, where a first state corresponds to when the second fluid is air, a second state corresponds to when the first fluid is air and the second fluid is oil, and a third state corresponds to when the first and second fluids are oil.

14. The engine oil system of claim 13 wherein the control module actuates the member, records the state of the oil condition sensing device, and then actuates the member.

15. The engine oil system of claim 14 wherein the control module, after recording the state and actuating the member, actuates the member until a change in the parameter is less than a predetermined threshold.

16. The engine oil system of claim 14 wherein the control module measures the oil viscosity level when the state of the oil condition sensing device is the third state.

17. The engine oil system of claim 14 wherein the control module identifies the oil change event when the state of the oil condition sensing device is the third state, the recorded state is the first state, and a value of the state of the oil condition sensing device from before a previous engine shutdown is one of the second and third states.

18. The engine oil system of claim 14 wherein the control module identifies the oil change event when the state of the oil condition sensing device is the third state and the recorded state is the first state.

19. The engine oil system of claim 18 wherein the oil condition sensing device includes a chamber with an opening that is sealed by an oil drain plug.

20. The engine oil system of claim 19 wherein the chamber is separated from a main portion of the engine oil reservoir by the first orifice.

21. The engine oil system of claim 20 wherein oil from the main portion is transferred to the chamber when the member is actuated.

22. The engine oil system of claim 21 wherein the second orifice is formed axially through the member.

23. A method comprising:
    selectively causing current to be supplied to an oil condition sensing device to actuate a member of the oil condition sensing device;
    measuring the current supplied to the oil condition sensing device;
    determining a parameter of the current; and
    selectively identifying at least two of an oil level, an oil change event, and an oil viscosity level based on the parameter.

24. The method of claim 23 wherein the parameter is based on a time of a local minimum of the current while the member is actuating.

25. The method of claim 24 wherein the parameter is based on a time delay between a trigger time and the time of the local minimum, wherein the current is caused to be supplied to the oil condition sensing device at the trigger time.

26. The method of claim 23 wherein the member is actuated to a first position when current is supplied and returns to a second position when current is not supplied.

27. The method of claim 23 wherein the oil level represents an oil level of an engine oil reservoir.

28. The method of claim 27 wherein the oil viscosity level represents an oil viscosity level of a sample of oil from the engine oil reservoir.

29. The method of claim 23 wherein the oil condition sensing device includes first and second orifices, and further comprising forcing a first fluid through the first orifice and a second fluid through the second orifice when the member is actuated.

30. The method of claim 29 further comprising determining that the first fluid is one of air and oil and that the second fluid is one of air and oil based on the parameter.

31. The method of claim 30 wherein the first orifice is positioned higher than the second orifice.

32. The method of claim 31 further comprising identifying the oil level as below a first predetermined level when the second fluid is air.

33. The method of claim 32 further comprising identifying the oil level as between the first predetermined level and a second predetermined level when the first fluid is air and the second fluid is oil, wherein the second predetermined level is greater than the first predetermined level.

34. The method of claim 33 further comprising identifying the oil level as above the second predetermined level when the first fluid and second fluids are oil.

35. The method of claim 30 further comprising determining a state of the oil condition sensing device, where a first state corresponds to when the second fluid is air, a second state corresponds to when the first fluid is air and the second fluid is oil, and a third state corresponds to when the first and second fluids are oil.

36. The method of claim 35 further comprising:
actuating the member;
recording the state of the oil condition sensing device resulting from the actuating; and
actuating the member after the recording.

37. The method of claim 36 further comprising, after recording the state and actuating the member, actuating the member until a change in the parameter between actuations is less than a predetermined threshold.

38. The method of claim 36 further comprising measuring the oil viscosity level when the state of the oil condition sensing device is the third state.

39. The method of claim 36 further comprising identifying the oil change event when the state of the oil condition sensing device is the third state, the recorded state is the first state, and a value of the state of the oil condition sensing device from before a previous engine shutdown is one of the second and third states.

40. The method of claim 36 further comprising identifying the oil change event when the state of the oil condition sensing device is the third state and the recorded state is the first state.

41. The method of claim 40 wherein the oil condition sensing device includes a chamber with an opening that is sealed by an oil drain plug.

42. The method of claim 41 wherein the chamber is separated from a main portion of an engine oil reservoir by the first orifice.

43. The method of claim 42 wherein oil from the main portion is transferred to the chamber when the member is actuated.

44. The method of claim 43 wherein the second orifice is formed axially through the member.

* * * * *